(12) United States Patent
Novak et al.

(10) Patent No.: US 8,025,672 B2
(45) Date of Patent: Sep. 27, 2011

(54) ULTRASONIC WOUND TREATMENT METHOD AND APPARATUS

(75) Inventors: Theodore A. D. Novak, Northport, NY (US); Mark Schafer, Ambler, PA (US); Ronald R. Manna, Valley Stream, NY (US)

(73) Assignee: Misonix, Incorporated, Farmingdale, NY (US)

( * ) Notice: Subject to any disclaimer, the term of this patent is extended or adjusted under 35 U.S.C. 154(b) by 103 days.

(21) Appl. No.: 11/511,853

(22) Filed: Aug. 29, 2006

(65) Prior Publication Data

US 2008/0058648 A1 Mar. 6, 2008

(51) Int. Cl.
*A61B 17/32* (2006.01)

(52) U.S. Cl. ...................................................... 606/169

(58) Field of Classification Search ................... 606/169, 606/128, 39, 40; 604/22; 600/471
See application file for complete search history.

(56) References Cited

U.S. PATENT DOCUMENTS

| | | | | |
|---|---|---|---|---|
| 5,527,273 A * | 6/1996 | Manna et al. | ............... | 604/22 |
| 5,540,693 A * | 7/1996 | Fisher | ............... | 606/79 |
| 5,836,897 A * | 11/1998 | Sakurai et al. | ............... | 601/2 |
| 5,935,142 A * | 8/1999 | Hood | ............... | 606/169 |
| 5,938,677 A * | 8/1999 | Boukhny et al. | ............... | 606/169 |
| 5,976,167 A * | 11/1999 | Lee | ............... | 606/189 |
| 6,083,191 A * | 7/2000 | Rose | ............... | 604/22 |
| 6,254,622 B1 * | 7/2001 | Hood | ............... | 606/169 |
| 6,773,443 B2 * | 8/2004 | Truwit et al. | ............... | 606/169 |
| 2002/0156466 A1 * | 10/2002 | Sakurai et al. | ............... | 606/1 |
| 2004/0030254 A1 | 2/2004 | Babaev | | |
| 2005/0096680 A1 * | 5/2005 | Zacharias | ............... | 606/169 |
| 2006/0229624 A1 * | 10/2006 | May et al. | ............... | 606/79 |
| 2008/0058775 A1 * | 3/2008 | Darian et al. | ............... | 606/1 |

FOREIGN PATENT DOCUMENTS

WO    WO 2007/143686    12/2007

* cited by examiner

*Primary Examiner* — Anhtuan Nguyen
*Assistant Examiner* — Sarah Simpson
(74) *Attorney, Agent, or Firm* — R. Neil Sudol; Henry D. Coleman; William J. Sapone

(57) ABSTRACT

A surgical device includes a probe, a transducer assembly operatively coupled to the probe for generating an ultrasonic resonant vibration therein, and a frequency generator operatively coupled to the transducer assembly for energizing the transducer component. A control component is operatively connected to the frequency generator for inducing the frequency generator to produce an alternating signal sequence including a first electrical excitation signal and a second electrical excitation signal, wherein the first electrical excitation signal has at least one first ultrasonic frequency and at least one first amplitude collectively selected to generate cavitation bubbles at a wound site to fragment damaged tissue and debride the wound site. The second electrical excitation signal has at least one second ultrasonic frequency and at least one second amplitude collectively selected to generate cavitation bubbles in a substantially reduced amount, thereby allowing for increased transmission of vibratory energy into the debrided tissues for enhancing healing.

14 Claims, 5 Drawing Sheets

ULTRASONIC WOUND TREATMENT METHOD AND APPARATUS

BACKGROUND OF THE INVENTION

This invention relates to ultrasonic surgical instruments and associated methods of use. More particularly, this invention relates to the treatment of wounds with ultrasound energy. The treatment contemplated by this invention includes fragmentation and emulsification of hard and soft tissue in a clinical environment while reducing unwanted heat and collateral tissue damage. In addition, the treatment includes therapy that improves the healing rate of the wound by stimulating the body's natural healing mechanisms.

Over the past 30 years, several ultrasonic tools have been invented which can be used to ablate or cut tissue in surgery. Such devices are disclosed by Wuchinich et al. in U.S. Pat. No. 4,223,676 and Idemoto et al in U.S. Pat. No. 5,188,102.

In practice, these surgical devices include a blunt tip hollow probe that vibrates at frequencies between 20 kc and 100 kc, with amplitudes up to 300 microns or more. Such devices ablate tissue by either producing cavitation bubbles which implode and disrupt cells, by generating tissue compression and relaxation stresses (sometimes called the jackhammer effect) or by other mechanisms such as micro streaming of bubbles in the tissue matrix. The effect is that the tissue becomes liquefied and separated. The fragmented tissue becomes emulsified with an irrigant solution. The resulting emulsion or slurry of tissue debris is then aspirated from the site. Bulk excision of tissue is possible by applying the energy around and under an unwanted tissue mass to separate it from the surrounding structure. The surgeon can then lift the separated tissue mass out using common tools such as forceps.

The tubular probe is excited by a transducer of either the piezoelectric or magnetostrictive type that transforms an alternating electrical signal within the frequencies indicated above into a longitudinal or transverse vibration. When the probe is attached to the transducer, the two become a single element with series and parallel resonances. The designer will try to tailor the mechanical and electrical characteristics of these elements to provide the proper frequency of operation. Most of the time, the elements will have a long axis that is straight and has the tip truncated in a plane perpendicular to the long axis, as shown in FIG. 1. This is done for simplicity and economic considerations. In almost all applications, whether medical or industrial, such an embodiment is practical and useful. However, in applications such as the debridement of burns, wounds, diabetic ulcers or ulcers induced by radiation treatments, the blunt straight probe has been shown to be less effective in removing the hard eschar buildup that occurs when the wound is healing. This eschar buildup must be removed so that the healthy tissue is exposed and allowed to close the wound to provide complete healing with minimal scar tissue formation. Also, the small diameter tip, since it is cannulated, has a small annular area with limits energy transmission into the wound. This extends the length of the procedure and causes operator fatigue and patient discomfort.

Therefore, it was desired to provide a probe that can be mated to an ultrasonic surgical aspirator that increases the efficiency of emulsification, does not heat up the operative site and lowers the time of operation.

In response to this need, a series of devices were developed which have been proven to address all of the shortcomings of the prior art and eliminate them. These devices are described in commonly owned copending U.S. application Ser. No. 11/087,451, filed Mar. 23, 2005. The devices have been shown to be effective in clinical use for the removal of necrotic tissue and hard eschar. The methods described in that prior application have also been shown to be efficacious in this regard.

However, the devices need to be driven at high excursion levels, i.e., high vibrational amplitudes, in order to effectively remove unwanted tissue. Once this tissue is removed, the high amplitudes can lead to higher pain perception on the part of the patient and can also lead to destruction of viable tissue if the operator is not careful. Also, the wound healing rates have been shown to be roughly the same as is observed after standard sharps debridement. An improvement in the healing rate that manifests itself as shorter time to heal is desired.

Therefore a need exists by which the probes described can be used whereby they will not increase wound pain and will also decrease healing time of the wound bed itself.

OBJECTS OF THE INVENTION

An object of the present invention is to provide an improved ultrasonic surgical instrument for use in wound treatment.

A more particular object of the present invention is to provide such an instrument that will improve wound healing times.

Another relatively specific object of the present invention is to provide an improved ultrasonic surgical instrument that enhances surgical efficiency and reduces the pain sensation of the patient.

It is a further object of the present invention to provide such an improved ultrasonic surgical instrument with irrigation or suction capability.

It is an additional object of the present invention to provide an improved ultrasonic surgical instrument that may be used in debriding deep wounds such as cuts and puncture wounds while improving healing rate.

These and other objects of the invention will be apparent from the drawings and descriptions herein. Although every object of the invention is attained in at least one embodiment of the invention, there is not necessarily any embodiment which attains all of the objects of the invention.

SUMMARY OF THE INVENTION

A probe for use as an ultrasonically vibrating tool is disclosed in the prior art with a central bore coincident with the longitudinal axis. The proximal end of said bore communicates with a bore in the ultrasonic handpiece using methods well known to the art, such as a male/female thread combination. The probe is shaped such as to provide both a resonant frequency of operation in the range for which the electronic generator was designed and an amplitude of vibration at the distal face which is desired for proper tissue ablation. Such amplitudes have generally been shown to be in the range of 30 to 300 microns.

Probe heads or ends in accordance with the prior art incorporate either a substantially symmetrical distal end or a distal end with a pronounced asymmetry. Each end has attributes that increase its effectiveness on varying tissue pathologies. Such probes improve the liquid flow to the probe/tissue interface such as to reduce the bulk temperature rise of the tissue and prevent clogging of the liquid passageway. Probe ends have been further modified to produce energy directors that impart energy from the sides of the probes instead of only at the distal face of the probe. Such energy directors, when contacting skin or tissue, will increase volume of tissue treated per unit time and thereby reduce the operating time of the procedure. A channel in the distal face of the probe was described in commonly owned copending U.S. application Ser. No. 11/087,451, filed Mar. 23, 2005, which allows liquid to flow from the central bore of the probe even when the distal surface is in contact with the wound. In this manner, constant contact between the probe end and the unwanted tissue may be obtained.

The theory of operation of these prior art devices is that the vibrating tip creates acoustic energy in the tissue or irrigation fluid in the form of cavitation or microstreaming. Such phenomenon has been well described in open literature for decades. This energy breaks up tissue and emulsifies it into the irrigant fluid, which can be aspirated from the wound site by standard means.

In order for this effect to take place, the amplitude of vibration of the tip must be high enough to create sufficient acoustic energy to induce cavitation. This is called the Cavitation Threshold. The amount of energy required and therefore the amount of tip displacement needed is variable from wound to wound. Amplitudes of 30 microns and above have been shown to create cavitation energy in most clinical settings, but vibrations below 30 have also been shown to create cavitation bubbles. Once a cavitation bubble is induced, enough energy exists at the probe wound interface to not only destroy tissue but to cause pain if the wound is debrided too deeply.

Once cavitation is induced, the resulting bubble shield will attenuate the transmission of acoustic waves into the body. This is due to the gaseous nature of the bubble cloud. It is well known that gas presents a high or infinite impedance to acoustic waves in the low ultrasound region.

If the probe operating face or energy director vibratory amplitude is less than that needed to induce cavitation, all of the acoustic energy is transmitted into the wound bed much the same way as an underwater speaker transmits sound waves. In this case, the tissues are being stressed by the compression and rarefaction waves. This movement stimulates the natural healing mechanisms of the body and increases the healing rate.

For instance, the low amplitude sonic waves (minimally or not occluded by the acoustic shield created by cavitation) has a benefit of repolarizing the cells, decongesting the wound bed, and disrupting the biofilm. The low acoustic energy also has been described as decongesting the wound and allowing factors critical to wound healing to reach the affected areas. In addition, this low frequency ultrasound appears to arrest the inflammation process minimizing the subsequent edema.

On moderate settings, i.e., at or very near the cavitation threshold, the acoustic energy results in moderate debridement of the wound, but the acoustic shield developed is not so great as to impede the majority or a substantial amount of the low amplitude waves from reaching the affected area. There is biofilm being destroyed and a significant amount of bacterial cell destruction taking place at these settings.

On the higher amplitude setting, the cavitation energy is substantially more aggressive with greater debridement evident. The acoustic wall created by the cavitation is so great that the low frequency waves are not present. The cavitation and microstreaming are removing devitalized tissue. The clinician may wish to treat the wound after this aggressive debridement with a low setting on the system to bathe the wound in greater low frequency waves.

In order to take advantage of this therapeutic effect of low amplitude waves, the present invention contemplates wound debridement with the electronic generator of the system set at an output that will give amplitudes of vibration significantly above the cavitation threshold. This will provide the most efficient debridement. Once the wound bed is debrided, the practitioner will reduce the amplitude of vibration of the system by turning the output signal lower, to a point below the cavitation threshold. The probe will then be rubbed on the debrided wound bed to allow the acoustic energy to flow into the wound without further debridement or tissue ablation. The levels of output may be marked as graduations on the rotary or linear output controls of the electronic generator to aid the practitioner in obtaining the proper settings.

In an alternative embodiment of the invention, the generator may incorporate a two position switch of any type such as, but not limited to, front panel rocker switch, footswitch controls, handpiece mounted switches, etc. The switches include a debridement setting or position and a therapy setting or position. Each setting, in turn, could optionally incorporate a fine adjustment control to tailor the output for that specific case. With this arrangement, the practitioner debrides the wound at the higher setting and then depresses the footswitch or other switch to change the output of the device to the lower setting. The probe is then rubbed over the clean wound bed to introduce acoustic energy into the site.

Alternatively or in conjunction with this embodiment, the output of the device may be automatically adjusted from the debridement setting to the therapy setting by means of modulating the output waveform of the electronic generator.

In this mode, the output of the generator is cycled from high setting output to low setting output by means of electronic or other means. Such means shapes the modulated wave with a substantially square wave modulation, a ramped modulation or sinusoid or other modulation which is practical. Time intervals for each wave section may be between 1 nanosecond to many minutes, depending upon the type of wound and clinical experience of the practitioner. In this manner, the practitioner sets the device to pulsed operation. The output of the unit provides high energy to debride the wound and then switches automatically to the low setting for a therapy mode. Here the practitioner continues rubbing the probe with direct contact on the wound bed. The wound is debrided initially and then is treated by the therapy mode without operator intervention. Some waveforms include a period where the output is totally off. This allows the tissue to relax and reach a normal state. When the ultrasound is reinitiated, the stress on the tissue is greater, increasing the therapeutic effect. It should be noted that any combination of debridement level time, therapeutic level time and off time is contemplated by this disclosure.

Another improvement relates to the frequency of operation of the ultrasonic wound debrider system. It is well known that different frequencies of operation have differing effects on the body. The lowest ultrasonic frequencies, approximately 16-20 KHz, create the highest cavitation effects and resulting debridement efficacy. The higher frequencies enhance the therapeutic effects of the device. Therefore different frequencies may be chosen for debridement and therapy.

It is well known in the ultrasound field that transducer and probes must be tuned to resonate at the desired operating frequency. Generally these items are tailored to have the fundamental half wave resonance at the frequency desired. They cannot generally be operated from a continuously variable frequency generator.

One embodiment of the present invention therefore includes two different transducers and probes, each tuned to a desired frequency for debridement and therapy, respectively. For example, one transducer may be tuned to 22.5 KHz and the other at 80 to 120 KHz. The electronic generator would incorporate circuitry to match the output to these transducers. The practitioner would then debride the wound with the lower frequency device and then switch to the higher frequency device for therapy. Each transducer could have a different output amplitude as well as frequency of operation. The method of use would be the same as the single frequency embodiment. One or both of the frequencies may be pulsed as in the original embodiment.

Switching between two different transducers, although practical and efficacious, could increase the time of operation, not to mention the higher cost of hardware if two or more transducers and probes are needed for each case.

In an alternative embodiment solving these extraneous issues, the electronic generator produces both (at different times) a fundamental frequency and a frequency that excites a harmonic or overtone of the original transducer and probe. Here the same transducer and probe could be used. When switched to therapy mode, the generator would find a resonant point of the transducer in the desired higher frequency band and provide the required output signal to cause vibrations at the probe distal end of sufficient amplitude for therapy. This could be pulsed and controlled in the same way as described above for the first embodiment (amplitude modification). The method of use is the same, in that the probe is placed into direct contact with the wound bed and the unit cycles from the debridement cycle or mode to the therapy cycle or mode either under practitioner control or by the automatic pulsing feature discussed above.

All of these vibratory modes may be present in a device that includes irrigation and aspiration features. Such irrigation may be through the center bore of a cannulated probe or from one bore of a multi channel probe. Conversely, it might be introduced coaxially by introducing the irrigant into the annular space between a sheath and the probe body. It could also be sprayed onto the sight from an outside irrigant source.

Likewise, aspiration may be provided by any of the means outlined for the irrigant. A separate aspiration wand may also be employed in lieu of integrating an aspiration channel into the transducer and/or probe.

A surgical method in accordance with the present invention comprises (a) placing an operative tip of an ultrasonic probe in contact with organic tissues of a patient at a wound site, (b) during the contacting of the tissues with the operative tip, energizing the probe to vibrate the operative tip at at least one first ultrasonic frequency and at least one first tip excursion amplitude preselected to generate cavitation bubbles, thereby fragmenting damaged tissue and debriding the wound site, and (c) subsequently, also during the contacting of the tissues with a working tip of an ultrasonic instrument, energizing the instrument to vibrate the working tip at at least one second ultrasonic frequency and at least one second tip excursion amplitude preselected to produce cavitation bubbles in a substantially reduced amount, thereby allowing for increased transmission of vibratory energy into the debrided tissues and enhancing healing.

Pursuant to a feature of the present invention, at least one of the second ultrasonic frequency and the second tip excursion amplitude is substantially different from the first ultrasonic frequency and the first tip excursion amplitude, respectively. Either the second tip excursion amplitude is substantially less than the first tip excursion amplitude, or the second frequency is substantially greater than the first frequency, the second frequency being an overtone or harmonic of the first frequency. Both conditions may also be met.

Pursuant to another feature of the present invention, where the ultrasonic instrument is the probe and the working tip is the operative tip, the energizing of the probe to vibrate the operative tip at the first ultrasonic frequency and the first tip excursion amplitude includes operating a frequency generator to produce a first excitation signal having the first ultrasonic frequency and a first signal amplitude resulting in the first tip excursion amplitude. The method further comprises activating a control device operatively connected to the frequency generator. Then the energizing of the probe to vibrate the operative tip at the second ultrasonic frequency and the second tip excursion amplitude includes operating the frequency generator, in response to the activating of the control device, to produce a second excitation signal having the second ultrasonic frequency and a second signal amplitude resulting in the second tip excursion amplitude.

The first ultrasonic frequency, the first signal amplitude, the second ultrasonic frequency, and the second signal amplitude may have predetermined or preset values so that successive activations of the control device cause a toggling between the first excitation signal and the second excitation signal. The surgeon merely presses a button or other switch to alternate between a debridement mode of operation and a therapy mode of operation.

Typically the frequencies and signal amplitudes are determined at the time of assembly of the probe and the frequency generator. However, the surgeon may be provided with the option of fine tuning the operating parameters. In that event, additional control devices are operatively connected to the frequency generator for modifying values of at least one of the first ultrasonic frequency, the first signal amplitude, the second ultrasonic frequency, and the second signal amplitude, and concomitantly, the first tip excursion amplitude and the second tip excursion amplitude.

In an alternative embodiment of the invention, where the ultrasonic instrument is the probe and the working tip is the operative tip, the alternating between a debridement mode and a therapy mode is accomplished automatically, i.e., without intervention by the surgeon, and in response to signals from a control unit, programmer, microprocessor, etc. In that case, the energizing of the probe to vibrate the operative tip at the first ultrasonic frequency and the first tip excursion amplitude includes operating a frequency generator to produce a first excitation signal having the first ultrasonic frequency and the first signal amplitude for a first duration, while the energizing of the probe to vibrate the operative tip at the second ultrasonic frequency and the second tip excursion amplitude includes operating the frequency generator to produce a second excitation signal having the first ultrasonic frequency and the first signal amplitude for a second duration. The method then further comprises operating the frequency generator to alternate between producing the first excitation signal and the second excitation signal.

In this alternative embodiment of the invention, the first ultrasonic frequency, the first signal amplitude, the second ultrasonic frequency, and the second signal amplitude may have predetermined or preset values.

In another alternative embodiment of the invention, where the ultrasonic instrument is the probe and the working tip is the operative tip, the alternating between a debridement mode and a therapy mode is also accomplished automatically, i.e., without intervention by the surgeon, and in response to signals from a control unit, programmer, microprocessor, etc. The instrument is the probe and the working tip is the operative tip. The energizing of the probe to vibrate the operative tip at the first ultrasonic frequency and the first tip excursion amplitude comprises operating a frequency generator to produce a varying excitation signal including the first ultrasonic frequency and a first signal amplitude at at least one point during an operating cycle. The varying excitation signal further includes the second ultrasonic frequency and a second signal amplitude at at least one point during the operating cycle.

The varying excitation signal may, for example, have a signal amplitude that in accordance with an alternating waveform such as a sawtooth waveform, a triangular wave, a square wave, a sinusoidal waveform, etc. The first and second excitation signals each recur at regular time intervals in an alternating fashion.

In an alternative embodiment of the method in accordance with the present invention, the probe and the instrument are different devices. The method then further comprises manipulating the probe to remove the operative tip from the organic tissues of the patient after the energizing of the probe at the first ultrasonic frequency and the first tip excursion amplitude, and manipulating the instrument to place the working tip into contact with the tissues after the removal of the operative tip and prior to the energizing of the instrument to vibrate the working tip at the second frequency and the second tip excursion amplitude. In other words, the surgeon replaces one tool with the other at the operating site.

The times of the debridement and the healing may be predetermined and timed by a timer. The timer may be triggered automatically or manually when the probe vibration and tissue contact first occur together for debridement. Similarly, the timer may be triggered automatically or manually when the instrument vibration and tissue contact first occur together for therapy. A buzzer or other alert signal may be generated to signal that the respective predetermined time interval has passed.

A surgical device in accordance with the present invention comprises a probe, a transducer assembly operatively coupled to the probe for generating an ultrasonic resonant vibration therein, a frequency generator operatively coupled to the transducer assembly for energizing the transducer component, and a control component operatively connected to the frequency generator for inducing the frequency generator to produce a varying excitation signal including at least a first electrical excitation signal and a second electrical excitation signal, wherein the first electrical excitation signal has at least one first ultrasonic frequency and at least one first amplitude collectively selected to generate cavitation bubbles at a wound site to fragment damaged tissue and debride the wound site, and wherein the second electrical excitation signal has at least one second ultrasonic frequency and at least one second amplitude collectively selected to generate cavitation bubbles in a substantially reduced amount, thereby allowing for increased transmission of vibratory energy into the debrided tissues for enhancing healing.

Preferably, the first ultrasonic frequency, the first amplitude, the second ultrasonic frequency and the second amplitude have predetermined values. Either the predetermined value of the first amplitude is substantially greater than the predetermined value of the second amplitude, and/or the predetermined value of the first ultrasonic frequency is substantially less than the predetermined value of the second ultrasonic frequency. In the latter event, the second ultrasonic frequency is an overtone or harmonic of the first ultrasonic frequency.

The control component may include a manually operable switch. Repeated operation of the manually operable switch may cause the frequency generator to alternate between the first excitation signal and the second excitation signal. The switch may have a first position for inducing generation of the first excitation signal and a second position for inducing generation of the second excitation signal. In addition, the control component may include controls for modifying the frequencies and amplitudes of the excitation signals.

In an alternative embodiment of the device, the control component includes a timing circuit for providing the first excitation signal with a first predetermined duration and the second excitation signal with a second predetermined duration. The timing circuit enables the frequency generator to alternate between producing the first excitation signal and the second excitation signal. The durations of these signals may vary from milliseconds or less to as much as a second or two. The surgeon may press a single control switch to activate the probe, which then automatically alternates between a debridement mode (first excitation signal) and therapy mode (second excitation signal).

In one particular embodiment of the present invention, the excitation waves and the motion of the operative or working tip of the probe are continuous. In the debridement operating mode, the frequency of the electrical excitation signal and concomitantly the frequency of vibration of the operative or working tip of the probe is 22 kc. The voltage applied to the transducer sets the amplitude of vibration (or the excursion of the tip) up to about 150 microns. In the wound treatment or therapy phase, the continuous wave frequency remains the same 22 kc while the excitation voltage is reduced to give an amplitude of tip vibration of less than 10 microns.

In another particular embodiment of the invention, where the excitation waveform and the probe tip excursion are continuous, the frequency of the electrical excitation signal and concomitantly the frequency of vibration of the operative or working tip of the probe in the debridement operating mode is 22 kc and the voltage applied to the transducer sets the amplitude of vibration (or excursion) of the probe tip up to about 150 microns. In the wound treatment or therapy phase of this second embodiment, the continuous wave frequency is increased to 88 kc while the excitation voltage is selected to give an amplitude of tip vibration of 10 microns or less.

Where switching between the debridement mode and the therapy mode is under automatic control, the excitation waveform can be generated with a pulsed envelope (sawtooth, square wave, sinusoid, etc.) wherein a continuous wave is periodically turned on and off (like an intermittent windshield wiper control) or high and low (max amplitude to minimum amplitude). The pulses may have, for example, a frequency of 10 times per second or 1 second duration or anything else to shape the continuous wave accordingly. The amplitude is the variable in the system, since the drive frequency for the transducer and probe would be the same.

DETAILED DESCRIPTION

Figure 1:
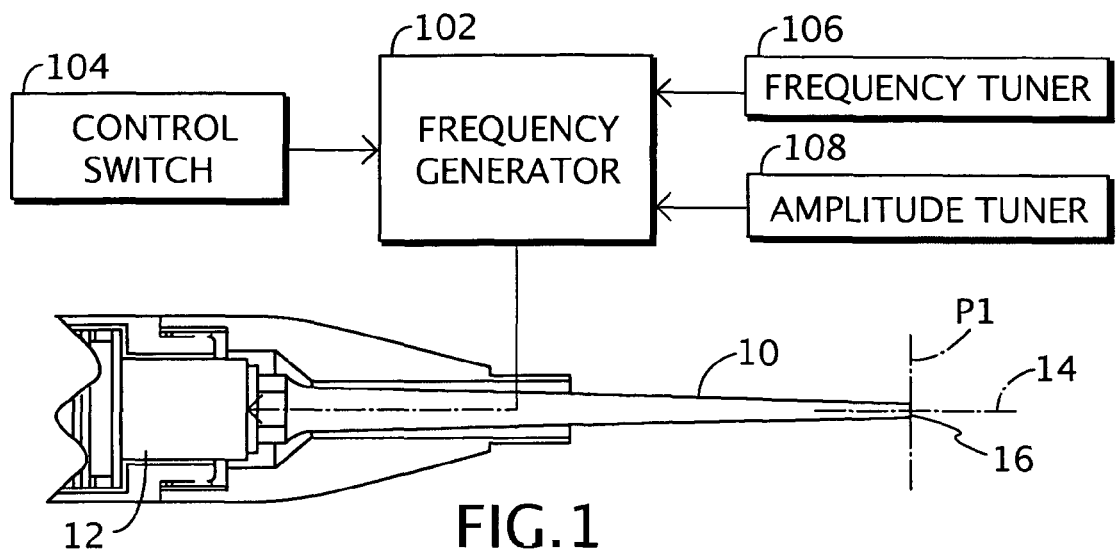
FIG. 1 is a cross sectional view of an ultrasonic probe for use with an ultrasonic aspirator, having frequency and amplitude control in accordance with the present invention.

Several probes are disclosed which embody the improvements described herein. FIG. 1 shows a probe 10 which is known to the art and is currently manufactured for use with an ultrasonic aspirator. This probe 10 is basically shaped with an exponential or Gaussian taper. Probe 10 is cannulated and has an integral male thread (not shown) at the proximal end (proximate the operator). This thread communicates with a female threaded bore (not illustrated) in the transducer 12. By tightening the probe 10 onto the transducer 12 and using standard wrenches for final torquing, the transducer and probe essentially become one resonant body. Bores of the probe 10 and transducer 12 communicate with one another. The probe 10 is generally constructed of an acoustically efficient metal or ceramic. Titanium is the most commonly used material, but other material has been employed with success. Material choice does not have a significant impact upon the embodiments of this disclosure.

The distal end of the prior art probe 10 is truncated in a plane P1 perpendicular to the longitudinal axis 14 of the resonant body (probe and transducer). Since the probe 10 is cannulated, a distal end face 16 takes the form of an annular surface with a small cross sectional area. The shape of the probe 10 allows the probe to become a velocity transformer, i.e., the probe will amplify the input vibrations from the transducer 12 by a fixed value, called a gain factor, determined by the geometry of the probe. For example, if the probe 10 had a gain factor of 10, the probe would multiply the input vibration of the transducer, for example 30 microns, to a final amplitude at the distal end of the probe of 300 microns. This phenomenon is well known to the art. By placing the distal end face 16 of probe 10 against organic tissue of a patient, the tissue will be disrupted through cavitation and mechanical effects. By adding saline or water to the tissue-probe interface, cooling of the tissue is achieved and the tissue is emulsified into the liquid and is more easily aspirated either through the center of the probe 10, if the center bore is connected to the aspirator or by separate suction cannulae if the center bore is connected to the irrigant source.

As shown in FIG. 1, transducer 12 may be connected to a frequency generator 102 that alternatively produces a first excitation signal for debridement and a second excitation signal for therapy. Frequency generator 102 may also produce, in an alternating sequence with the first excitation (debridement) signal and the second excitation (therapy) signal, an off signal of limited duration for temporarily halting the vibration of probe 10.

Frequency generator 102 receives a control signal from a control switch 104 of any type such as, but not limited to, front panel rocker switches, footswitch controls, handpiece mounted switches, etc. A surgeon operates switch 104 to toggle the output of frequency generator 102 between the debridement signal and the therapy signal.

The debridement signal and the therapy signal are each characterized by a respective frequency and a respective amplitude. The debridement signal has either an amplitude that is substantially higher than the amplitude of the therapy signal or a frequency that is substantially lower than that of the therapy signal or both. In any case the output frequency of the generator 102 is matched to the resonant frequency (or a harmonic) of the probe 10. For instance, the debridement signal may have a frequency of 22.5 KHz and such an amplitude as to cause an excursion of 50 or 60 microns of distal end face 16 of probe 10. The therapy signal produced by generator 102 may have the same frequency and a smaller amplitude, causing an excursion of 30 microns or less of probe end face 16. Alternatively or additionally, the therapy signal may have a frequency of 90 or 112.5 KHz (harmonics of 22.5 KHz).

As further shown in FIG. 1, tuning controls 106 and 108 may be provided. Tuning controls 106 and 108 are operatively connected to frequency generator 102 for enabling a surgeon to make fine adjustments in the magnitudes of the output frequency and amplitude, respectively.

Frequency generator 102, control switch 104, and tuning controls 106 and 108 may be used with any of the probes described herein, as well as any other probes designed for debriding soft or hard organic tissues.

It is to be noted that the distal end of probe 10 in its conventional configuration is not conducive to ablating large volumes of tissue in short periods of time. By increasing the surface area of distal end face 16, a probe can be constructed which will ablate tissue faster and allow for a shorter operation. This is especially advantageous when debriding wounds such as bedsores, diabetic ulcers, burn wounds, etc.

Figure 2A:
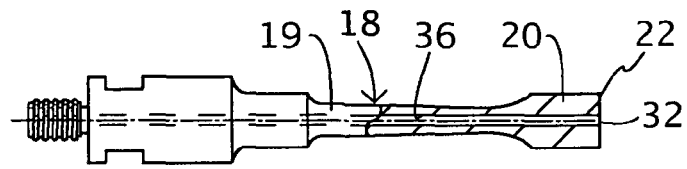
FIG. 2A is partially a side elevational view and partially a cross-sectional view of another ultrasonic probe utilizable with frequency and amplitude control in accordance with the present invention.
Figure 2C:
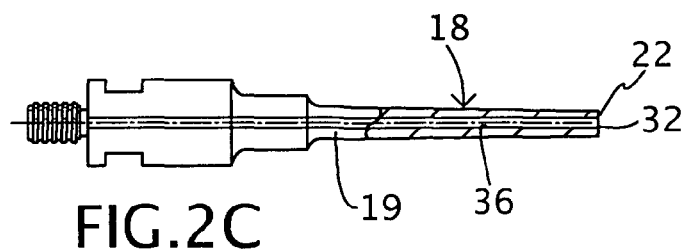
FIG. 2C is partially a top elevational view and partially a cross-sectional view of the probe of FIG. 2A.
Figure 2B:
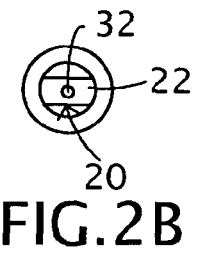
FIG. 2B is a distal end elevational view of the probe of FIG. 2A.

FIGS. 2A-2C show a probe 18 with a shaft 19 and an enlarged distal head 20. More particularly, probe head 20 may be asymmetrical such that the cross sectional shape is rectangular or oval (see FIG. 2B). This asymmetry allows the probe 18 to maintain a higher gain factor and be more able to be inserted into smaller wounds. The surface area of a distal end face 22 of probe head 20 is greatly increased over the prior art probe (FIG. 1) and will naturally ablate tissue at a higher rate. The shape of the probe head 20 allows access to irregularly shaped wound beds, such as cuts or fissures with slit openings.

Figure 3A:
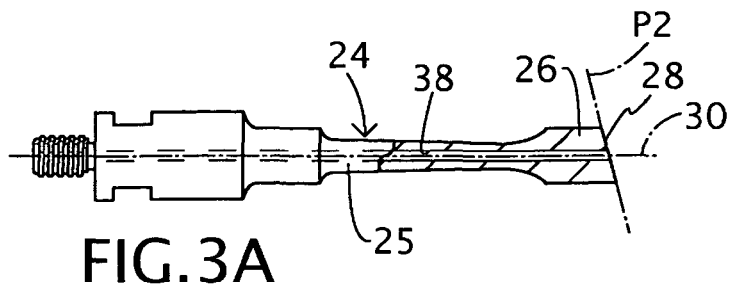
FIG. 3A is partially a side elevational view and partially a cross-sectional view of another ultrasonic probe utilizable with frequency and amplitude control in accordance with the present invention.

Although the probe of FIGS. 2A-2C has been shown to have higher performance over prior art, further improvements may be made. FIG. 3A depicts a probe 24 having a shaft 25 and an asymmetrically enlarged head 26 with a truncated or beveled distal end face 28 located in a plane P2 that is not perpendicular to a longitudinal axis 30 of the probe. This probe 24 has been shown to improve performance in removing the hard eschar buildup of burn wounds, which must be removed in order to expose healthy tissue.

One problem that is encountered in such probe designs, whether the probe head is truncated in a perpendicular plane P1 such as head 20 or in a plane P2 inclined relative to the instrument axis 30 such as probe head 26, is the bore opening 32 or 34 may become blocked with tissue. This blockage prevents aspiration of the emulsified tissue, if the respective bore 36 or 38 is connected to a vacuum source (not shown) or blocks the flow of cooling fluid out of the probe, if the bore is attached to a pressurized liquid source (not shown). Because of the pressure buildup, the liquid has a tendency to jet or stream from the probe tissue interface, causing the irrigant to be sprayed around the room instead of onto the wound bed. Also, if the distal end face of the probe is very large, the liquid may not cover the entire face, even if the opening 32, 34 at the end of the probe is not blocked.

Figure 3C:
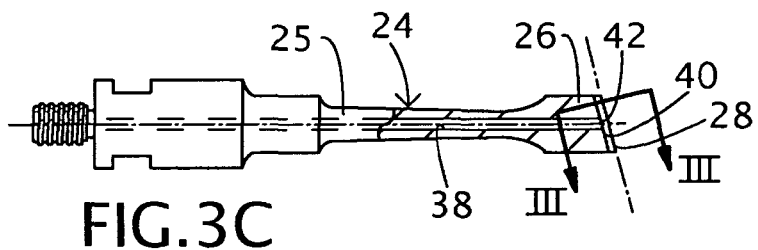
FIG. 3C is a view similar to FIG. 3A showing the groove of FIG. 3B.
Figure 3B:
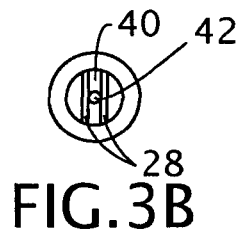
FIG. 3B is a distal end elevational view of the probe of FIG. 3A, showing a modification in the form of an elongate groove in a distal end face of the probe head.
Figure 3D:
FIG. 3D is a partial cross-sectional view taken along line III-III in FIG. 3C.

In order to improve the performance of the probe 24 in this regard, a channel, groove, indentation, or notch 40 is provided in the face 28 of the probe, as shown in FIG. 3B, 3C and 3D. This channel 40 reduces the likelihood of blockage of an output opening 42 of the probe bore 38 by locating this opening or outlet proximally from the distal end face 28 of the probe head 26, while allowing the liquid to fill the channel 40 and cover the remaining distal surface area more fully. Many alternative shapes of channels may be employed in the distal end faces of ultrasonic probes without changing the concepts outlined herein. In the illustrated example, channel or groove 40 extend parallel to or in a length dimension of the end face 28.

When bore 38 is connected to a suction source (not shown), fluid in the channel 40 flows toward the bore 38. When the channel or bore 38 is connected to a source of irrigation liquid (not shown), liquid in the channel 40 flows away from the bore 38.

Regardless of the shape of the distal surface or end faces of the probes as discussed hereinabove, the probes are limited in their ability to ablate tissue by the fact the only area where this ablation can occur is at the distal end face. The sides or lateral surfaces of the probes are generally disposed parallel to the longitudinal axes and parallel to the direction of ultrasonic compression wave transmission. When tissue touches these lateral surfaces, no ablation occurs since the motion is a sliding or rubbing action, which does not transmit sufficient energy into the tissue to cause emulsion or ablation. It is therefore desired to improve ultrasonic tissue ablation probes so that energy may be transmitted from one or more lateral faces or side surfaces of the probe heads so that more tissue may be ablated per unit time.

Figure 4:
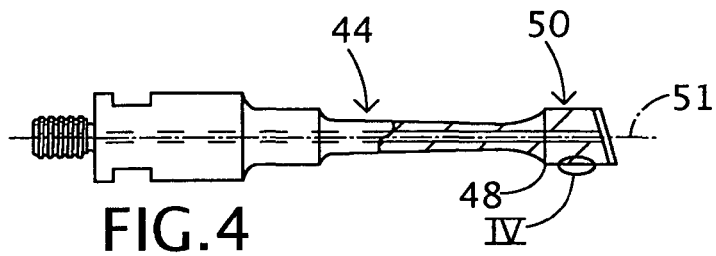
FIG. 4 is partially a side elevational view and partially a cross-sectional view of a further ultrasonic probe utilizable with frequency and amplitude control in accordance with the present invention.
Figure 4A:
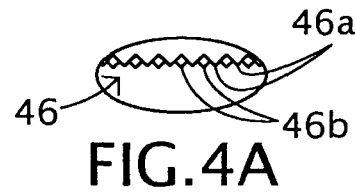
FIG. 4A is partial view, on a larger scale, of a lateral surface of a head of the probe of FIG. 4, taken in region IV-IV of FIG. 4.

FIGS. 4 and 4A show a probe 44 which is identical to probe 24 of FIGS. 3B-3D with the addition of outwardly or radially extending projections 46 serving as energy guides or directors disposed along at least one lateral or side surface 48 of a probe head 50. Preferably, probe head 50 has a prismatic shape with four planar lateral surfaces or faces 48, projections 46 being disposed only along one or two of the lateral surfaces. As depicted in FIG. 4, energy-directing projections 46 are disposed only along two opposing lateral surfaces 48. Where projections occur along only one or at most two lateral surfaces 48, it is easier for the user to avoid contact with non-target tissues.

Probe head 50 may be integrally formed with a shaft portion 49 of probe 44. Alternatively, probe head 50 may be formed as a separate piece that is firmly attached to shaft 49, e.g., via mating screw threads (not shown) or a force or friction fit. These same alternatives also apply to probe heads 20, 26, 66.

Figure 4B:
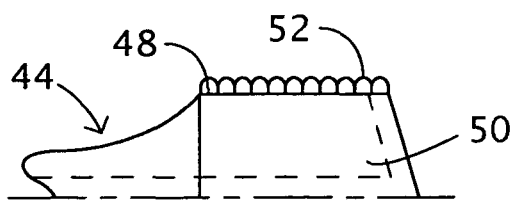
FIGS. 4B-4D are side elevational views of the probe head of FIG. 4, showing respective modifications of formations along the lateral surface thereof.
Figure 4C:
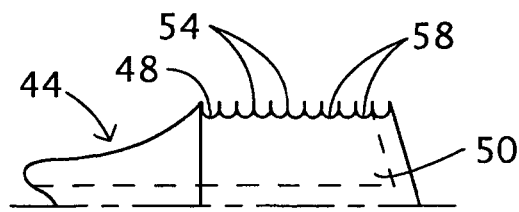
Figure 4D:
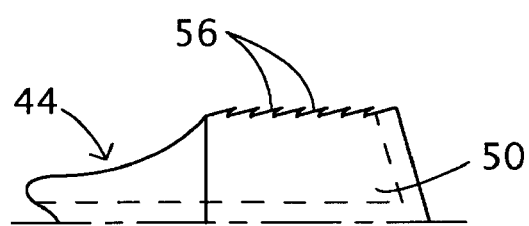
Figure 4E:
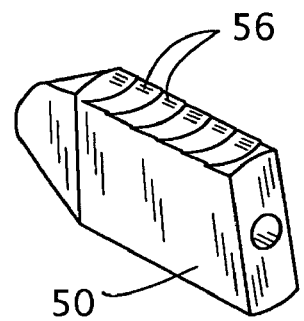
FIG. 4E is a perspective view of the probe head depicted in FIG. 4D.

Projections 46 may have a fine geometrical configuration and distribution so as to form the respective lateral surface 48 into a knurled surface as one would find, for example, on a metal file. Or projections 46 may be a series of ridges or knurls on probe head 50. Alternatively, as shown in FIG. 4B, projections or energy directors 46 may be pyramidal sections fashioned from the base metal of the probe 44 that project out in a substantially perpendicular direction from a longitudinal axis 51 of the probe. More specifically, projections or energy directors 46 are a series of parallel ridges or knurls each of triangular cross-section extending transversely to a direction of ultrasonic wave propagation. Projections or energy directors 46 may include a first set of parallel ridges 46a and a second set of ridges 46b that is staggered relative to the first set. Each set of wedge- or triangle-shaped projections or ridges 46a, 46b defines a corresponding set of grooves (not separately designated) each of triangular cross-section extending transversely to a direction of ultrasonic wave propagation. The resulting faceted surfaces of projections or ridges 46a, 46b impart a vector force on the target tissue when the probe 44 vibrates, which will cause cavitation and emulsification of the tissue when it contacts the faceted surfaces.

As illustrated in FIGS. 4B-4E, lateral surface 48 may be provided with energy-directing projections or ridges 52, 54, 56 of different geometrical shapes. Projections or ridges 52 are convex, for instance, semi-cylindrical. Projections or ridges 54 define concave grooves or recesses 58. Projections 56 are flattened plates or flaps that lie against lateral surface 48 in the natural of fish scales. These energy directors or projections 52, 54, 56 allow faster tissue ablation by creating a much larger active surface area at the distal end of the probe 44.

Figure 5:
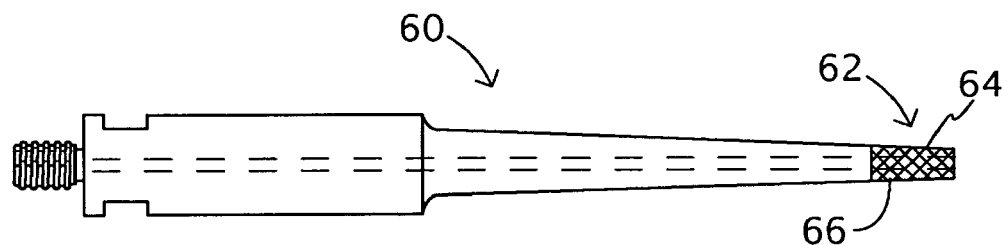
FIG. 5 is partially a side elevational view and partially a cross-sectional view of yet another ultrasonic probe utilizable with frequency and amplitude control in accordance with the present invention.

In cases where a probe tip must be smaller than that allowed by the described embodiment, such as when small and/or deep bedsores or wounds must be debrided, the probe tip may be improved to allow faster ablation as well. FIG. 5 shows a probe 60 in the configuration of a tubular end or head 62. Probe 60 is provided circumferentially along a cylindrical lateral or side surface 64 or probe head 62 with a plurality of pyramidal energy-directing projections 66. Projections 66 may be small such as that which occurs in a knurled surface, for example, on a metal file. The energy directors 66 will impart vector forces on the tissue when in contact with the wound bed such that emulsion and ablation will occur around the probe as well as in front of it. Such probes have been shown to increase the speed of ablation and thereby significantly reduce the time of operation. Again, such energy directors may be purely pyramidal, or have concave or convex faces.

All said probes in this embodiment might be designed by those skilled in the art using known tools and techniques.

In a method of using the above-described probes for debriding and cleaning wounds, sores and ulcers with ultrasound energy, an operator assembles the ultrasonic surgical aspirator with the probes, connects the central bore to a pressurized liquid source which can be adjusted to provide a controlled flow at the probe tip, turn on the system to provide between 30 and 350 microns of probe tip displacement, and touches the tip and the energy directors to the tissue to be ablated, causing cavitational and mechanical forces to be imparted to said tissue which ablates the tissue, thereby debriding and cleansing the wound bed. Aspiration may be accomplished simultaneously or separately from ultrasonic ablation by connecting a flue or sheath around said probe, as in FIG. 6, that is in turn connected to a vacuum source and then the emulsified tissue is aspirated through this annular space. Conversely, the flue or sheath may be eliminated and the aspirate removed via separate suction cannulae.

A surgical method utilizing probe 24 or 44 or another probe provided in an end face with a channel, groove, indentation, or notch such as channel 40 is operated to vibrate at an ultrasonic frequency. The distal end face 22, 28 of the probe is brought into contact with organic tissues of a patient. The probe is energized to ultrasonically vibrate the end face 22, 28 during the contacting of the tissues with the distal end face, and liquid is channeled between the contacted tissues and longitudinal bore 36, 38, during the contacting of the tissues with the distal end face, via indentation or channel 40.

A surgical method utilizing probe 44 or 60 comprises bringing the lateral surface 48 or 64 together with projections, ridges, or knurls 46, 66 into contact with organic tissues of a patient and, during the contacting of the tissues with the lateral surface and the projections, energizing the probe to vibrate the lateral surface 48, 64 and the projections 46, 66 at a predetermined ultrasonic frequency. This method may include inserting a distal end portion of the probe into a cut, fissure or recess in an organ of the patient and moving the probe so that the lateral surface 48, 64 and the projections 46, 66 contact a wall of the fissure or recess.

Alternatively or additionally, the probe is manipulated so that the lateral surface 48, 64 is oriented substantially parallel to the organic tissues and so that the distal end face is oriented substantially perpendicularly to the organic tissues immediately prior to an engaging of the organic tissues with the lateral surface 48, 64 and the projections 46, 66.

Figure 6:
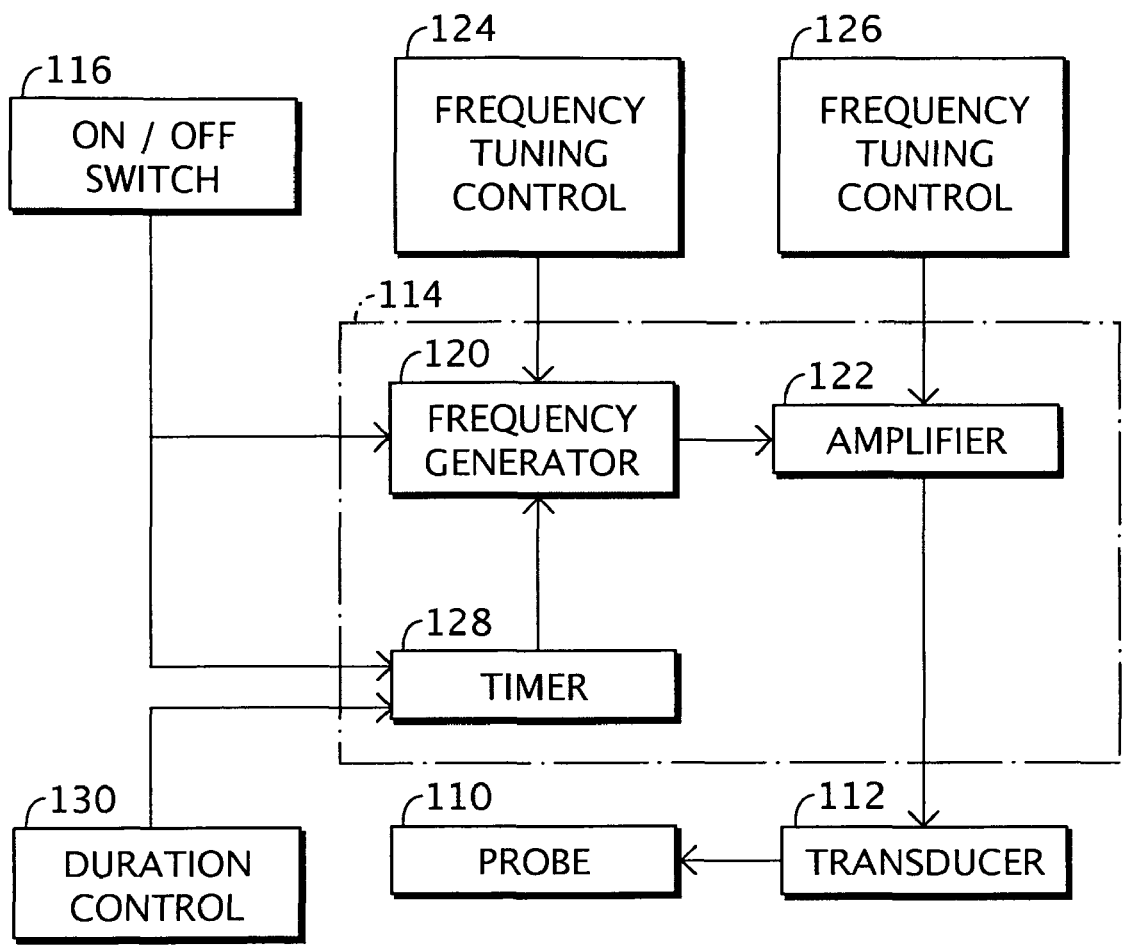
FIG. 6 is a block diagram of another ultrasonic wound debridement probe assembly or system in accordance with the present invention.

FIG. 6 diagrammatically depicts an ultrasonic surgical device that produces an alternating sequence of vibratory modes automatically without the necessity for operator intervention. The vibratory modes include at least a cavitation or debridement mode and a vibration transmission or therapy mode. Optionally, the alternating sequence includes an off cycle or mode, wherein prove vibration is halted. These vibratory modes may occur with predetermined durations ranging from a nanosecond to several seconds or even minutes.

The surgical device of FIG. 6 comprises a probe 110, a transducer assembly 112 operatively coupled to the probe for generating an ultrasonic resonant vibration therein, a frequency generator unit 114 operatively coupled to the transducer assembly for energizing the transducer component, and a control component or switch 116 operatively connected to the frequency generator for inducing the frequency generator to produce an alternating sequence including a first electrical excitation signal and a second electrical excitation signal. The first electrical excitation signal has an ultrasonic frequency and an amplitude collectively selected to generate cavitation bubbles at a wound site to fragment damaged tissue and debride the wound site. The second electrical excitation signal has an ultrasonic frequency and an amplitude collectively selected to generate cavitation bubbles in a substantially reduced amount, thereby allowing for increased transmission of vibratory energy into the debrided tissues for enhancing healing. In addition, an off signal (zero amplitude) may be fed to transducer 112 by frequency generator unit 114 over a lead 118 as a component of the alternating sequence including the first and second excitation signals.

Typically, the operative or working tip of probe 10 vibrates at the same frequency as the excitation signal, while the amplitude of vibration of the operative or working probe tip is mainly determined by the amplitude of vibration of the excitation signal. While the amplitude of the excitation signal may be predetermined in certain instruments, the amplitude of tip vibration will vary depending on load and other factors. The frequency generator unit 114 of FIG. 6 particular includes a frequency generator 120 and an amplifier 122. Tuning controls 124 and 126 are operatively connected to generator 120 and amplifier 122 for enabling a surgeon or other operator to optimize the frequency and amplitude values. Frequency generator unit 114 may optionally include a timer 128 for determining the durations of the excitation signals ad the off signal, if any. A duration control 130 is operatively connected to timer 128 for enabling the surgeon or other operator to modify the durations of the excitation signals and the off signal, if any.

The first and second excitation signals (debridement and therapy) may have frequency and/or amplitude values that vary during the operation of the surgical device of FIG. 6. In particular, the output signal of frequency generator unit 14, on lead 118, may be a continuous waveform wherein frequency and/or amplitude varies continuously between a debridement range of values ("D" high to "D" low in FIG. 7) and a therapy range of values ("T" high to "T" low in FIG. 7). For instance, the amplitude of the output signal on lead 118 may vary in a continuous curve, such as a sawtooth (FIG. 7), a ramped signal (not illustrated), a square wave (not illustrated), etc. Periods of no amplitude (off signal) may be interspersed at intervals in the otherwise continuous waveform.

Figure 7:
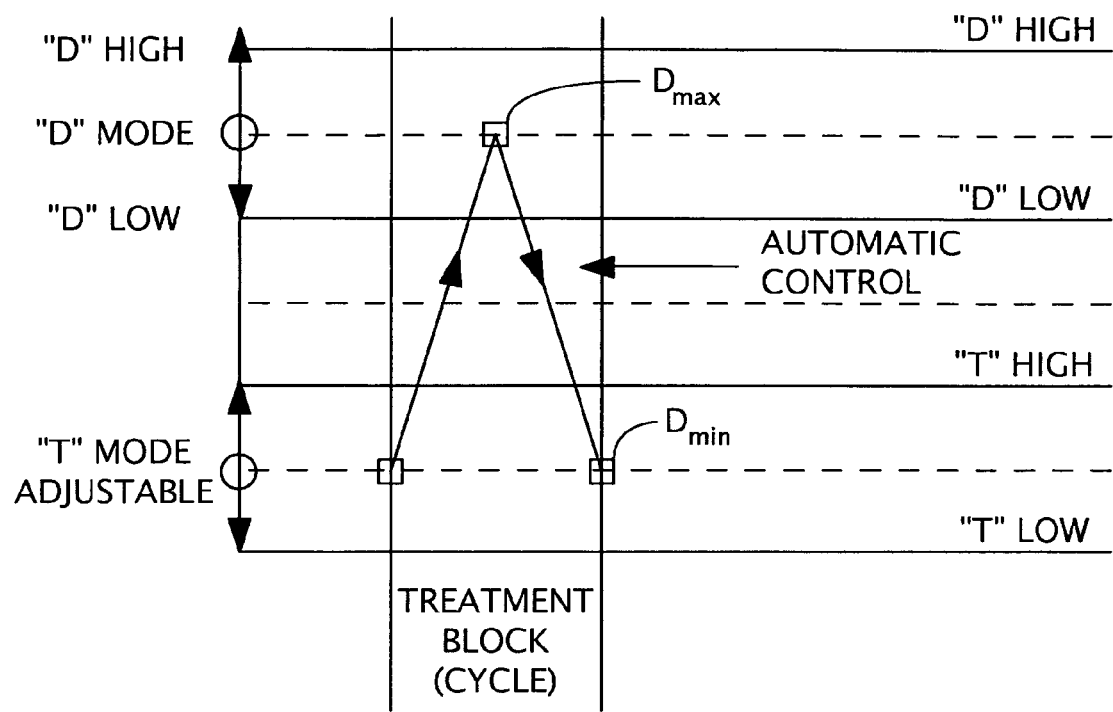
FIG. 7 is a graph showing a mode of operation of the ultrasonic wound debridement probe assembly of FIG. 6.

The frequencies and amplitudes of the excitation signals have predetermined maximum and minimum values as shown in FIG. 7. When the varying parameter (frequency or amplitude) has a value in the debridement range, between "D" high and "D" low, cavitation bubbles are generated at a wound site in an amount effective to fragment tissue and emulsify damaged tissue. When the varying parameter (frequency or amplitude) has a value in the therapy range, between "T" high and "T" low, cavitation bubbles are generated at a wound site in such a reduced amount that the ultrasonic vibrations are transmitted into the tissues at the wound site to stimulate or promote the healing process.

FIG. 7 shows a predetermined maximum value $D_{max}$ for the amplitude of the first excitation (debridement) portion of the output signal on lead 118 and a predetermined minimum value $D_{min}$ for the amplitude of the second excitation (debridement) portion of the output signal of frequency generator unit 114. Amplitude maximum $D_{max}$ is substantially greater than amplitude minimum $D_{min}$. Where the frequency varies between the debridement portion of the excitation signal and the therapy portion of the excitation signal, the frequency minimum of the debridement portion is substantially less than the frequency maximum of the therapy portion of the excitation signal. The frequency maximum is an overtone or harmonic of the frequency minimum.

Switch 116 is a manually operable switch that turns on the device, e.g., enabling the frequency generator 114. The surgeon may press control switch 116 to activate the probe, which then automatically alternates between the debridement mode (first excitation signal) and therapy mode (second excitation signal).

In the continuous signal embodiment of the surgical device of FIG. 6, timer 128 may function to vary, for example, the rate at which the signal changes between the minimum and maximum points, thus controlling the durations of the debridement portion and the therapy portion of the excitation signal. More complexity in the continuous signal function can be used to provide different proportions of time in the debridement and the therapy modes. The durations of the debridement and therapy portions of the excitation signal may vary from a nanosecond to as much as several seconds or minutes.

In using the ultrasonic device of FIG. 6, the surgeon places an operative tip of probe 110 in contact with organic tissues of a patient at a wound site. During the contacting of the tissues with the operative tip, probe 110 is energized by frequency generator unit 114 to vibrate the operative tip at amplitudes within the debridement range "D" high to "D" low and alternately therewith at amplitudes in the therapy range "T" high to "T" low. Cavitation bubbles are generated during operation in the debridement range, thereby fragmenting damaged tissue and debriding the wound site. In the therapy range, cavitation bubbles are produced in a substantially reduced amount, thereby allowing for increased transmission of vibratory energy into the debrided tissues and enhancing healing.

Tuning control 126 enables the surgeon or user to modify minimum value $D_{min}$ and maximum value $D_{max}$. Where the frequency of the excitation signal is different in the debridement and excitation portions of the signal, tuning control 124 may be used to modify minimum and maximum values of the frequency. Generally, the selected minimum and maximum are in a range close about natural or resonant frequencies of vibration of probe 110.

The present invention additionally contemplates a combined wound debridement and therapy procedure wherein one or more surgeons use two different ultrasonic surgical tools, a first probe operating in a debridement mode and a second probe or instrument operating in a therapy mode. The surgeon or surgeons use the debridement probe on a trauma site for a time adequate to remove necrotic tissue from the site and then use the therapy instrument on the debrided tissue to stimulate a healing response. The duration or interval that the therapy instrument's working tip is in contact with the debrided tissue surface may be timed by a timer.

It is to be noted that the application of ultrasonic energy, whether in the debridement mode or the therapy mode, may be effectuated continuously or in pulses, regardless of whether one or two probes are used. The pulses may be of short duration, on the order of milliseconds or less, with inter-pulse intervals of similar duration, or may be as long as a second or two. Of course, the inter-pulse intervals may have durations that differ from the pulse durations.

Also, where a pulsatile mode is used, the ultrasonic instrument may be provided with controls for modifying the durations of the pulses and the inter-pulse intervals, pursuant to the exigencies of the moement as determined by the surgeon.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A surgical method comprising:
providing an ultrasonic probe having a shaft and a probe head that is enlarged relative to said shaft in a direction transverse to a longitudinal axis of said shaft, said probe head being provided with a substantially planar lateral surface extending generally parallel to said longitudinal axis of said shaft, said lateral surface being laterally outwardly spaced relative to said shaft;
placing said lateral surface in contact with organic tissues of a patient at a wound site;
during the contacting of the tissues with said lateral surface, energizing the probe to vibrate said probe head at at least one first ultrasonic frequency and at least one first tip excursion amplitude preselected to fragment damaged tissue and debride the wound site by generation of cavitation bubbles; and
subsequently, also during a contacting of the tissues with said probe head, energizing the probe to vibrate said probe head at at least one second ultrasonic frequency and at least one second tip excursion amplitude preselected for increased transmission of vibratory energy into the debrided tissues and enhancing healing, wherein said second ultrasonic frequency is substantially greater than said first ultrasonic frequency and wherein said second tip excursion amplitude is substantially less than said first tip excursion amplitude, said first ultrasonic frequency being a low frequency and said first tip excursion amplitude being a high amplitude, said second ultrasonic frequency being a high frequency and said second tip excursion amplitude being a low amplitude.

2. The method defined in claim 1 wherein said second frequency is an overtone or harmonic of said first frequency.

3. The method defined in claim 1 wherein said instrument is said probe and said working tip is said operative tip, the energizing of said probe to vibrate the operative tip at said first ultrasonic frequency and said first tip excursion amplitude includes operating a frequency generator to produce a first excitation signal having said first ultrasonic frequency and a first signal amplitude resulting in said first tip excursion amplitude, further comprising activating a control device operatively connected to said frequency generator, the energizing of said probe to vibrate the operative tip at said second ultrasonic frequency and said second tip excursion amplitude including operating said frequency generator, in response to the activating of said control device, to produce a second excitation signal having said second ultrasonic frequency and a second signal amplitude resulting in said second tip excursion amplitude.

4. The method defined in claim 3 wherein said first ultrasonic frequency, said first signal amplitude, said second ultrasonic frequency, and said second signal amplitude have predetermined or preset values so that successive activations of said control device cause a cycling among a plurality of signals including said first excitation signal and said second excitation signal.

5. The method defined in claim 4 wherein said plurality of signals includes an off signal so that vibration of said probe is at least slowed or retarded between a period of generation of said first excitation signal and a period of generation of said second excitation signal.

6. The method defined in claim 3, further comprising additional control devices operatively connected to said frequency generator for modifying values of at least one of said first ultrasonic frequency, said first tip excursion amplitude, said second ultrasonic frequency, and said second tip excursion amplitude.

7. The method defined in claim 1 wherein said instrument is said probe and said working tip is said operative tip, the energizing of said probe to vibrate the operative tip at said first ultrasonic frequency and said first tip excursion amplitude includes operating a frequency generator to produce a first excitation signal having said first ultrasonic frequency and a first signal amplitude for a first duration, the energizing of said probe to vibrate the operative tip at said second ultrasonic frequency and said second tip excursion amplitude including operating said frequency generator to produce a second excitation signal having said second ultrasonic frequency and a second signal amplitude for a second duration, further comprising operating said frequency generator to automatically alternate between producing said first excitation signal and said second excitation signal.

8. The method defined in claim 7 wherein said first ultrasonic frequency, said first signal amplitude, said second ultrasonic frequency, and said second signal amplitude have predetermined or preset values.

9. The method defined in claim 7 wherein the operating of said frequency generator to alternate between producing said first excitation signal and said second excitation signal includes operating said frequency generator to produce an off signal having a third duration for temporarily halting vibration of said probe.

10. The method defined in claim 1 wherein said instrument is said probe and said working tip is said operative tip and wherein the energizing of said probe to vibrate the operative tip at said first ultrasonic frequency and said first tip excursion amplitude comprises operating a frequency generator to produce a varying excitation signal including said first ultrasonic frequency and a first signal amplitude at at least one point during an operating cycle, said varying excitation signal further including said second ultrasonic frequency and a second signal amplitude at at least one point during said operating cycle.

11. The method defined in claim 10 wherein said varying excitation signal has a signal amplitude that in accordance with an alternating waveform.

12. The method defined in claim 1 wherein said probe and said instrument are different devices, further comprising manipulating said probe to remove said operative tip from said tissues after the energizing of said probe at said first ultrasonic frequency and said first tip excursion amplitude, and manipulating said instrument to place said working tip into contact with said tissues after the removal of said operative tip and prior to the energizing of said instrument to vibrate said working tip at said second frequency and said second tip excursion amplitude.

13. The method defined in claim 12, further comprising operating a timer to set a first duration that said operative tip is vibrated in contact with said tissues and a second duration that said working tip is vibrated in contact with said tissues.

14. The method defined in claim 1 wherein said lateral surface is provided with a planar array of projections adapted to enhance debridement of organic tissues.

* * * * *